United States Patent
Poirier et al.

(10) Patent No.: US 11,717,145 B2
(45) Date of Patent: Aug. 8, 2023

(54) METHOD FOR PLACEMENT OF AN IMAGING ELEMENT CLEANING APPARATUS AND OBTURATOR FOR ENABLING SAME

(71) Applicant: ClearCam Inc., Austin, TX (US)

(72) Inventors: David K. Poirier, Houston, TX (US); Douglas G. Stoakley, Austin, TX (US)

(73) Assignee: ClearCam Inc., Austin, TX (US)

( * ) Notice: Subject to any disclaimer, the term of this patent is extended or adjusted under 35 U.S.C. 154(b) by 302 days.

(21) Appl. No.: 17/221,865

(22) Filed: Apr. 5, 2021

(65) Prior Publication Data

US 2021/0386281 A1    Dec. 16, 2021

Related U.S. Application Data

(62) Division of application No. 16/900,715, filed on Jun. 12, 2020, now Pat. No. 11,033,179.

(51) Int. Cl.
*A61B 1/12*     (2006.01)
*B08B 9/043*    (2006.01)
*A61B 90/70*    (2016.01)

(52) U.S. Cl.
CPC .............. *A61B 1/126* (2013.01); *A61B 1/123* (2013.01); *B08B 9/0436* (2013.01);
(Continued)

(58) Field of Classification Search
CPC ..... A45C 11/043; A61C 17/00; A61B 1/0125; A61F 2/16; B28B 7/381; G02C 13/008
(Continued)

(56) References Cited

U.S. PATENT DOCUMENTS 5,392,766 A    2/1995  Masterson et al.
5,518,502 A    5/1996  Kaplan et al.
(Continued)

FOREIGN PATENT DOCUMENTS

CN    101883531 B    7/2014
EP      0647425 A1   4/1995
(Continued)

OTHER PUBLICATIONS

International Search Authority, Notification of Transmittal of the International Search Report and Written Opinion of the International Search Authority, PCT/US2019/063369, 16 pages.

*Primary Examiner* — Monzer R Chorbaji
(74) *Attorney, Agent, or Firm* — David O. Simmons; I VC Patent Agency

(57) ABSTRACT

Embodiments of the present invention provide a method, system and assembly each adapted for enabling an imaging element cleaning apparatus to be placed through an abdominal wall of the patient without the use of a trocar or cannula. By eliminating the need for and use of a cannular or trocar, such embodiments advantageously overcome dimensional compatibility issues exhibited between the inside diameter of the central passage of commercially-available trocars and cannulas and the outside diameter of the sheath of an imaging element cleaning apparatus comprising such a sheath. Such dimensional compatibility issues are overcome by enabling an imaging element cleaning apparatus of the present disclosures to be placed through the abdominal wall of a patient without the use of a trocar or cannula. As a result, the sheath of the aforementioned imaging element cleaning apparatus can be in direct contact with the abdominal wall tissue.

20 Claims, 7 Drawing Sheets

(52) U.S. Cl.
CPC ..... *A61B 2090/701* (2016.02); *A61L 2202/17* (2013.01); *A61L 2202/24* (2013.01)

(58) Field of Classification Search
USPC ......................................................... 600/127
See application file for complete search history.

(56) References Cited

U.S. PATENT DOCUMENTS

| | | |
|---|---|---|
| 6,755,782 B2 | 6/2004 | Ogawa |
| 6,923,759 B2 | 8/2005 | Kasahara et al. |
| 7,543,314 B2 | 6/2009 | Kadykowski |
| 7,959,561 B2 * | 6/2011 | Akui .................. A61B 1/00087 600/157 |
| 8,690,764 B2 | 4/2014 | Clark et al. |
| 8,979,738 B2 | 3/2015 | Hsu et al. |
| 9,486,129 B2 | 11/2016 | Rodriguez Sanjuan |
| 9,763,567 B2 | 9/2017 | O'Prey et al. |
| 2009/0250081 A1 | 10/2009 | Gordin et al. |
| 2012/0101338 A1 | 4/2012 | O'Prey et al. |
| 2014/0094650 A1 | 4/2014 | Schaning |
| 2017/0332893 A1 | 11/2017 | Irion et al. |
| 2017/0367571 A1 | 12/2017 | Nave |

FOREIGN PATENT DOCUMENTS

| | | |
|---|---|---|
| JP | S5861723 A | 4/1983 |
| JP | H01204637 A | 8/1989 |
| JP | 04-362912 | 12/1992 |
| JP | H05103748 A | 4/1993 |
| JP | 2015031026 A | 2/2015 |
| JP | 5735908 B2 | 6/2015 |
| WO | 200912587 A2 | 10/2009 |
| WO | 2014034839 A1 | 3/2014 |
| WO | WO2017006684 | 12/2017 |

* cited by examiner

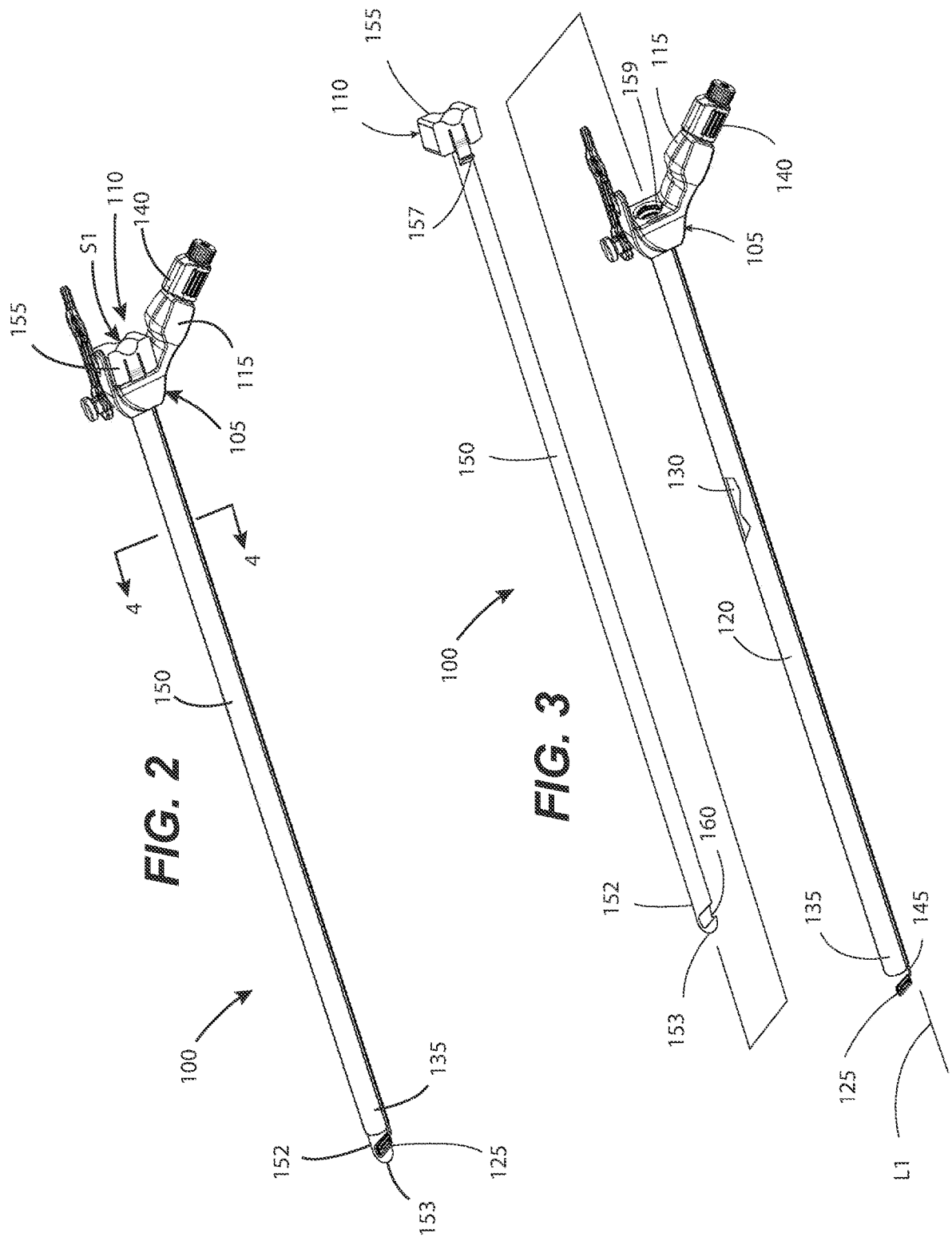

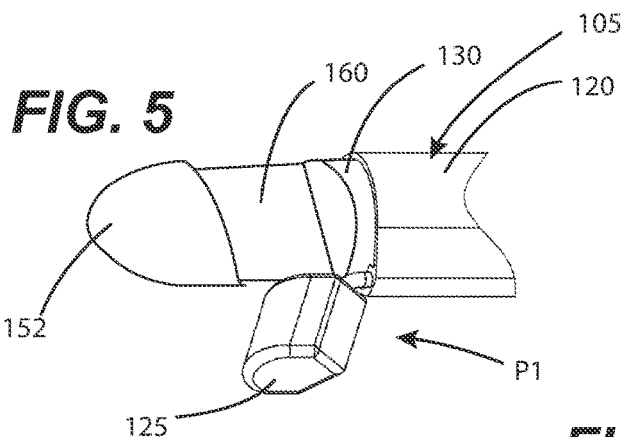
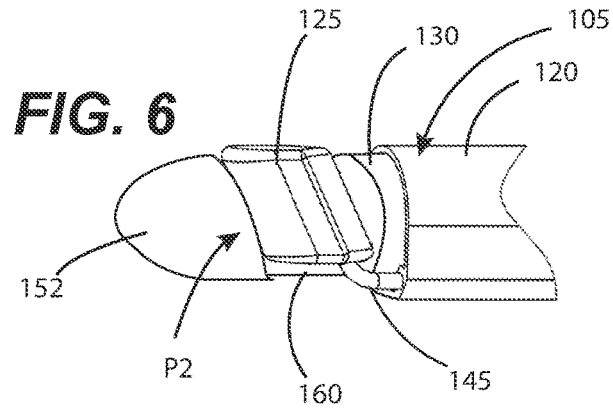
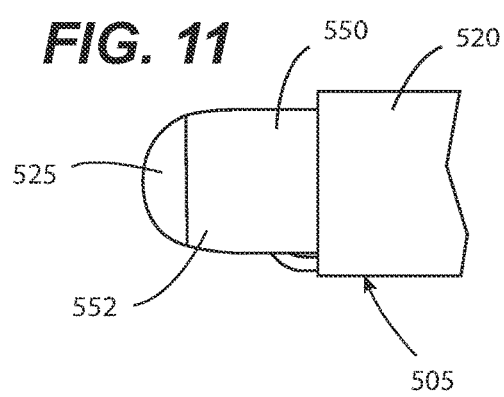
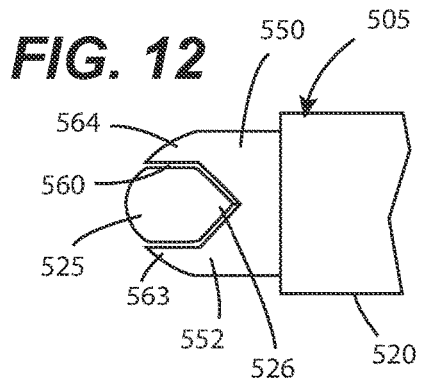
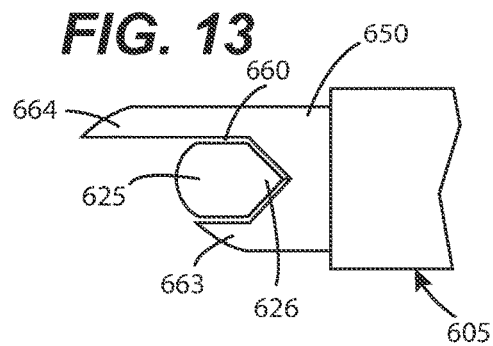

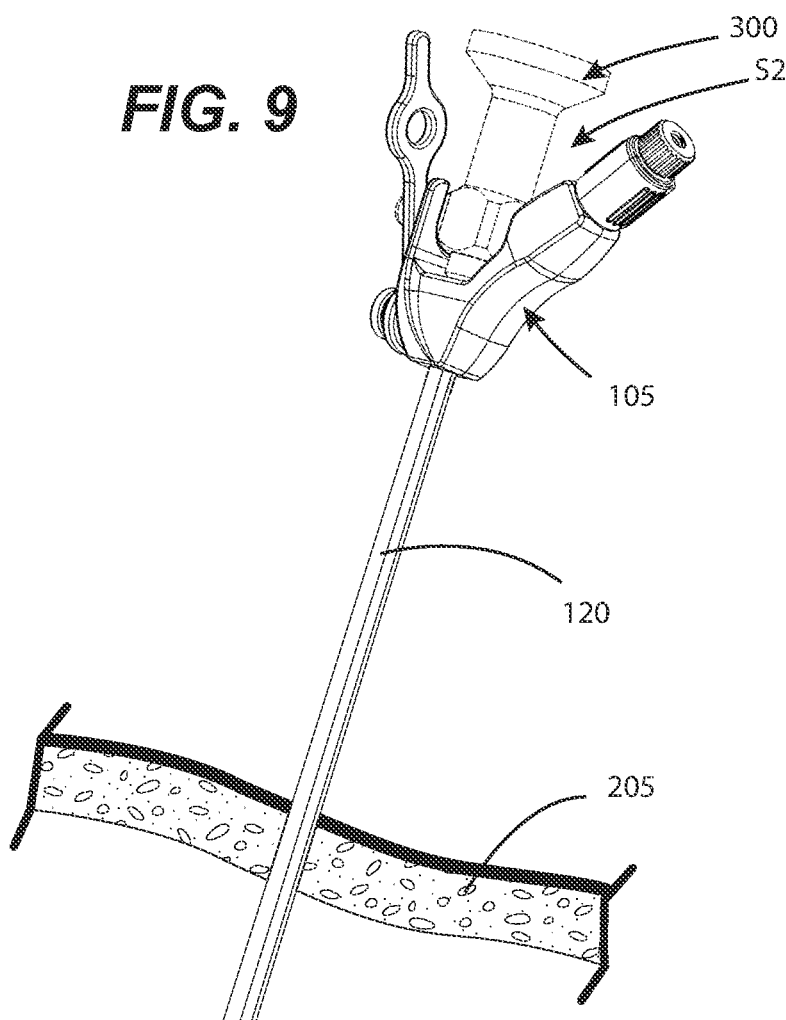
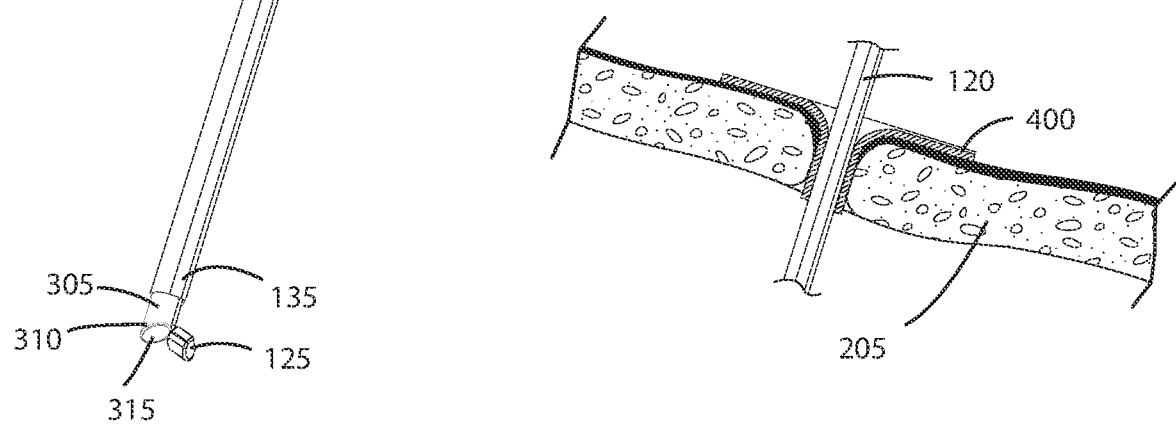

METHOD FOR PLACEMENT OF AN IMAGING ELEMENT CLEANING APPARATUS AND OBTURATOR FOR ENABLING SAME

CROSS-REFERENCE TO RELATED APPLICATIONS

This patent application claims priority as a divisional from co-pending U.S. Non-Provisional patent application Ser. No. 16/900,715, filed 12 Jun. 2020, entitled "METHOD FOR PLACEMENT OF AN IMAGING ELEMENT CLEANING APPARATUS AND OBTURATOR FOR ENABLING SAME", which has a common applicant herewith and being incorporated herein in its entirety by reference.

FIELD OF THE DISCLOSURE

The disclosures made herein relate generally to cleaning of devices that utilize a remote imaging element for visualization of structures at a concealed site and, more particularly, to an imaging element cleaning apparatus for cleaning an exposed surface of the imaging element while the exposed surface is located within a concealed site such as an in vivo human or animal environment.

BACKGROUND

Surgical procedures utilizing in vivo visualization of target surgical sites are well known as a form of a concealed operation site. Examples of these surgeries include, but are not limited to, endoscopic surgery, laparoscopic surgery, thoracoscopic surgery and the like. These surgical procedures all utilize a surgical instrument having an integrated visualization device for providing in vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope".

As shown in FIG. 1, an endoscope 1 used in these surgical procedures is characterized as having a user interface portion 5 and an extension portion 10 connected at its proximate end 15 to the user interface portion 5. Scopes for endoscopic surgery generally have an extension portion that is substantially flexible, whereas scopes for other types of surgical procedures—e.g., for laparoscopic surgery, as shown in FIG. 1—generally have an extension portion 10 that is substantially rigid. The extension portion 10 has an imaging element 20 such as a lens at its distal end portion 25. The imaging element 20 can have an exposed surface that is typically generally flush with or that defines an end face of the extension portion 10. The imaging element 20 is connected to an optical fiber or other image transmitting element that is internal to the endoscope. The optical fiber or other image transmitting element extends along the length of the extension portion 10 and terminates at an eyepiece 30 on the user interface portion 5. The eyepiece 30 enables the imaging element 30 to be connected to a visualization device (e.g., a camera connected to a visual display console) through which target surgical sites can be viewed by surgery personnel.

During a surgical procedure using an endoscope, the exposed surface of the imaging element thereof may become impaired due to one or more in vivo scenarios. Examples of these scenarios include the exposed surface of the imaging element becoming fogged with moisture within the surgical space, or the exposed surface of the imaging element may be smeared by blood or other bodily fluids or tissues (e.g. interstitial fluid, fat tissue or the like). Currently, there are two primary different endoscope cleaning methods that are commonly utilized. The first of these cleaning methods is to remove the endoscope from the body, wipe the imaging element clean, and reinsert the endoscope into the body. This method, though effective, is time consuming and causes the surgeon to lose visual of the surgical site, which can be considered dangerous, as surgical instruments typically remain inside the body. This method can also subject the patient to a higher risk of infection. The second of these cleaning methods is to wipe the exposed surface of the imaging element upon a nearby organ or tissue. Although the endoscope remains inside the body, takes less time to clean and does not potentially compromise the surgical site, this method is often not sufficiently effective either due to the "cleaning" surface not providing effective cleaning performance or simply further contaminating the exposed surface of the imaging element. Also, when using either of these cleaning methods, the surgeon must undesirably spend time relocating the endoscope to the surgical site after cleaning the imaging element.

At a minimum, current approaches for cleaning the exposed surface of the imaging element can be a hindrance and an annoyance for surgeons and may offer poor cleaning performance. Additionally, the action of cleaning the exposed surface of the imaging element increases the length of time a surgical procedure takes, thereby decreasing the amount of operating room (OR) time available to the hospital. It is also costly for hospitals, patients, and insurance companies due to wasted time, and possibly surgical complications and post-surgical infection rates. Additionally, as patients undergo longer procedures, their time spent under anesthesia increases. Increased time under anesthesia has been shown to correlate to a rise in surgical complication rates and post-surgical infection rates. Thus, the added time associated with current commonly used approaches for cleaning the exposed surface of the imaging element is not only a hindrance, but also potentially medically and financially costly.

Thus, to maintain required visualization of target surgical sites, it is desirable to clean an exposed surface of an imaging element of a device while the distal end portion of the device remains in a concealed operation site (e.g., an endoscope in vivo). Known methods and devices that are intended to provide for cleaning of a surface of such devices when still within the concealed operation site (e.g., an endoscope in vivo) have one or more shortcomings (e.g., lack efficacy, interfere with the surgical procedure, require significant alteration to a surgeon's preferred surgical technique, etc.). Therefore, an effective, efficient, simple and reliable approach for allowing an exposed surface of an imaging element of device (e.g., an endoscope) to be cleaned while the distal end portion of apparatus is still within the concealed operation site (e.g., in vivo) would be advantageous, desirable and useful.

SUMMARY OF THE DISCLOSURE

As is well known in the art, an extension portion of an endoscope (e.g., a laparoscope or other form of an endoscope) extends through a central passage of a trocar, cannula or combination thereof, which itself extends through the abdominal wall of a patient for enabling placement of a lens of the endoscope within an abdominal cavity of the patient. To this end, a first well-known function of a trocar is providing a sealed interface with the abdominal wall for limiting (and preferably inhibiting) escape of gaseous material (e.g., insufflation gas) from within the abdominal cavity through the interface between tissue of the abdominal wall and the trocar. A second well-known function of a trocar is providing a sealed interface with the extension portion of the endoscope for limiting (and preferably inhibiting) escape of the gaseous material from within the abdominal cavity through the interface between imagining element device and the trocar. However, as is also well known in the art, the inside diameter dimension of the central passage of trocars can vary by brands and/or models, and the outside diameter dimension of the extension portion of endoscopes can similarly vary by brands and/or models. As such, compatibility between trocars and endoscopes (and other similar types of imaging devices) used therewith can be limited by such dimensional variations.

Imaging element cleaning apparatuses of the present disclosures comprise a sheath adapted to receive a lens-carrying elongated portion of an endoscope the device. Examples of such imaging element cleaning apparatuses are disclosed in U.S. patent application Ser. No. 16/593,150; U.S. Pat. Nos. 7,547,314 and 6,923,759 and Japanese Publication No. JP04-362912, all of which are incorporated herein in their entirety by reference. The sheath is thin-walled to permit its insertion through commercially-available trocars and cannulas. Much like the dimensional compatibility issues of endoscopes and trocars/cannulas, the sheath of such an imaging element cleaning apparatus can similarly exhibit dimensional compatibility issues due to the outside diameter of the sheath being slightly greater than the outside diameter of the lens-carrying elongated portion of an endoscope and thus larger than the inside diameter of some commercially-available trocars/cannulas.

Advantageously, embodiments of the present invention overcome such dimensional compatibility issues of an imaging element cleaning apparatus of the present disclosures by eliminating the need for and use of a cannular or trocar. To this end, embodiments of the present invention are directed to providing an effective, predictable and reliable approach for enabling placing through an abdominal wall of a patient an imaging element cleaning apparatus utilized for cleaning an exposed surface of the imaging element (e.g., a lens) of an endoscope (i.e., an imaging device) while the distal end portion thereof (i.e., the lens carrying end portion thereof). More specifically, embodiments of the present invention provide a method and cleaning apparatus system configured for enabling such method to be performed in a manner whereby an imaging element cleaning apparatus of the present disclosures can be placed through the abdominal wall of the patient without the use of a trocar or cannula. As opposed to a cannular and/or trocar providing the interface between the abdominal wall tissue and the imaging element cleaning apparatus, a sheath of the aforementioned imaging element cleaning apparatus can be in direct contact with the abdominal wall tissue (e.g., the fascial tissue), whereby such direct engagement of the abdominal wall tissue with the exterior surface of the sheath forms a leak-proof or leak-resistant seal therebetween. Such omission of the cannula and trocar is desirable as it eliminates adverse issue associated with dimensional incompatibilities and eliminates the need to devise a trocar and/or cannula specifically designed for precluding or at least mitigating such dimensional incompatibilities associated with an imaging element cleaning apparatus of the present disclosures.

In one or more embodiments of the present invention, an endoscope cleaning system comprises an endoscope cleaning apparatus and an obturator. The endoscope cleaning apparatus includes a sheath and a cleaning member. The sheath includes a central passage adapted for having an elongated member of an endoscope disposed therein. The cleaning member is located at a distal end portion of the sheath. The cleaning member is movably attached to the sheath to permit selective movement of the cleaning member over a central passage opening at the distal end portion of the sheath. The obturator includes a head and a shank attached at a proximate end portion thereof to the head. The shank is removably engageable within the central passage of the sheath through a central passage opening at a proximate end portion of the sheath. A distal tip portion of the shank has a space therein adapted for receiving therein at least a portion of the cleaning member. A length of the shank is sufficient for enabling the distal tip portion of the shank to extend beyond the central passage opening of the sheath at the distal end portion thereof when the obturator is in a seated position relative to the endoscope cleaning apparatus.

In one or more embodiments of the present invention, an endoscope placement assembly comprises an endoscope cleaning apparatus and an obturator. The endoscope cleaning apparatus includes a sheath and a cleaning member. The sheath includes a central passage. The cleaning member is located at a distal end portion of the sheath and is movably attached to the sheath to permit selective movement of the cleaning member over a central passage opening at the distal end portion of the sheath. The obturator includes a head and a shank attached at a proximate end portion thereof to the head. The obturator is in a seated position on the endoscope cleaning apparatus with a shank of the obturator positioned within a central passage of a sheath of the endoscope cleaning apparatus. A distal tip portion of the shank protrudes from within the central passage of the sheath at a distal end portion thereof. At least a portion of the cleaning member is positioned within a cleaning member receiving receptacle at the distal tip portion of the shank.

In one or more embodiments of the present invention, a method is provided for placing an endoscope through an abdominal wall of a patient. A step is performed for providing an endoscope placement assembly comprising an imaging element cleaning apparatus and an obturator. The obturator is in a seated position on the imaging element cleaning apparatus with a shank of the obturator positioned within a central passage of a sheath of the imaging element cleaning apparatus. A distal tip portion of the shank protrudes from within the central passage of the sheath at a distal end portion thereof. At least a portion of the cleaning member is positioned within a cleaning member receiving space at the distal tip portion of the shank. One or more steps are performed for forming an incision within an abdominal wall of a patient, engaging a tissue penetrating structure of the endoscope placement assembly with the incision and applying pressure to the endoscope placement assembly to force the tissue penetrating structure of the endoscope placement assembly through the incision and cause the sheath to extend through the abdominal wall. Thereafter, one or more steps are performed for detaching the obturator from the imaging element cleaning apparatus and mating an endoscope with the imaging element cleaning apparatus after detaching the obturator such the endoscope is in a seated position on the imaging element cleaning apparatus with an elongated member of the endoscope disposed within the central passage of the sheath and a distal end portion of the elongated member of the endoscope protruding from the distal end portion of the sheath adjacent to a cleaning member of the imaging element cleaning apparatus.

It is an object of one or more embodiments of the present invention for at least a portion of an exterior surface of the sheath to be treated to promote low friction engagement with abdominal wall tissue.

It is an object of one or more embodiments of the present invention for at least a portion of said cleaning member receiving space to be within a side surface of the shank.

It is an object of one or more embodiments of the present invention for a surface of the distal tip portion of the shank defines a tissue penetrating structure of the obturator.

It is an object of one or more embodiments of the present invention for at least a portion of said cleaning member receiving space to be within an end face of the shank.

It is an object of one or more embodiments of the present invention for a rear face of the cleaning member to at least partially defines a tissue penetrating structure of the obturator.

It is an object of one or more embodiments of the present invention for said cleaning member receiving space to bisects the distal tip portion of the shank and interior surfaces of said cleaning member receiving space are configured to follow a contour of a lens wiping portion of the cleaning member.

It is an object of one or more embodiments of the present invention for a depth of said cleaning member receiving space to be greater than a depth of the cleaning member such that an entire portion of the cleaning member is within said cleaning member receiving space.

It is an object of one or more embodiments of the present invention for a rear face of the cleaning member and one or more surfaces of the distal tip portion of the shank to each be contoured to jointly form a tissue penetrating structure of the obturator.

It is an object of one or more embodiments of the present invention for providing the endoscope placement assembly to include rotating the cleaning member of the imaging element cleaning apparatus to a rotational obturator installing position enabling the obturator to be mounted on the imaging element cleaning apparatus in the seated position without the shank inhibiting said mounting and mounting the obturator on the imaging element cleaning apparatus in the seated position while the cleaning member is in the rotational obturator installing position.

It is an object of one or more embodiments of the present invention for at least a portion of said cleaning member receiving space to be within a side surface of the shank and for providing the endoscope placement assembly to include rotating the cleaning member of the imaging element cleaning apparatus to a rotational obturator installing position in which the obturator can be mounted on the imaging element cleaning apparatus in the seated position without the shank contacting the cleaning member during said mounting, mounting the imaging element cleaning apparatus on the imaging element cleaning apparatus in the seated position while the cleaning member is in the rotational obturator installing position and rotating the cleaning member to an assembly use position in which at least a portion of the cleaning member is within a cleaning member receiving space of the shank.

It is an object of one or more embodiments of the present invention for at least a portion of said cleaning member receiving space to be within a side surface of the shank and for detaching the obturator from the central passage of the sheath to include rotating the cleaning member to an obturator detachment position in which the shank can be withdrawn from within the central passage of the sheath without the shank contacting the cleaning member during said withdrawal of the shank and pulling on the head of the obturator until the shank is fully withdrawn from within the central passage of the sheath.

These and other objects, embodiments, advantages and/or distinctions of the present invention will become readily apparent upon further review of the following specification, associated drawings and appended claims.

BRIEF DESCRIPTION OF THE DRAWINGS

FIG. 2 is a perspective view showing a cleaning apparatus system in accordance with a first embodiments of the present invention.

FIG. 3 is exploded view of the cleaning apparatus system of FIG. 2, showing an imaging element cleaning apparatus and obturator thereof.

FIG. 5 is a partial perspective view showing a distal end portion of the cleaning apparatus system of FIGS. 2 and 3, showing a cleaning member of the imaging element cleaning apparatus displaced from within a cleaning member receiving space of the obturator.

FIG. 6 is a partial perspective view showing the distal end portion of the cleaning apparatus system of FIGS. 2 and 3, showing the cleaning member of the imaging element cleaning apparatus rotated into the cleaning member receiving space of the obturator.

FIG. 9 is a diagrammatic side view showing the sheath of the imaging element cleaning apparatus of FIG. 8 extending through the abdomen wall of the patient with an endoscope engaged within the sheath.

FIG. 10 is a diagrammatic side view showing an embodiment of an access site sealing element used in conjunction a cleaning apparatus system in accordance with one or more embodiments of the present invention.

FIG. 11 is partial top view of a cleaning apparatus system in accordance with a second embodiments of the present invention, showing relative positioning of a cleaning member of an imaging element cleaning apparatus of the cleaning apparatus system within a cleaning member receiving space defined by equal length protruding legs of an obturator shank.

FIG. 12 is partial side view of the cleaning apparatus system of FIG. 11, showing relative positioning of the cleaning member within the cleaning member receiving space.

FIG. 13 is partial side view of a cleaning apparatus system in accordance with a third embodiments of the present invention, showing relative positioning of a cleaning member of an imaging element cleaning apparatus of the cleaning apparatus system within a cleaning member receiving space defined by different length protruding legs of an obturator shank.

DETAILED DESCRIPTION

Figure 1:
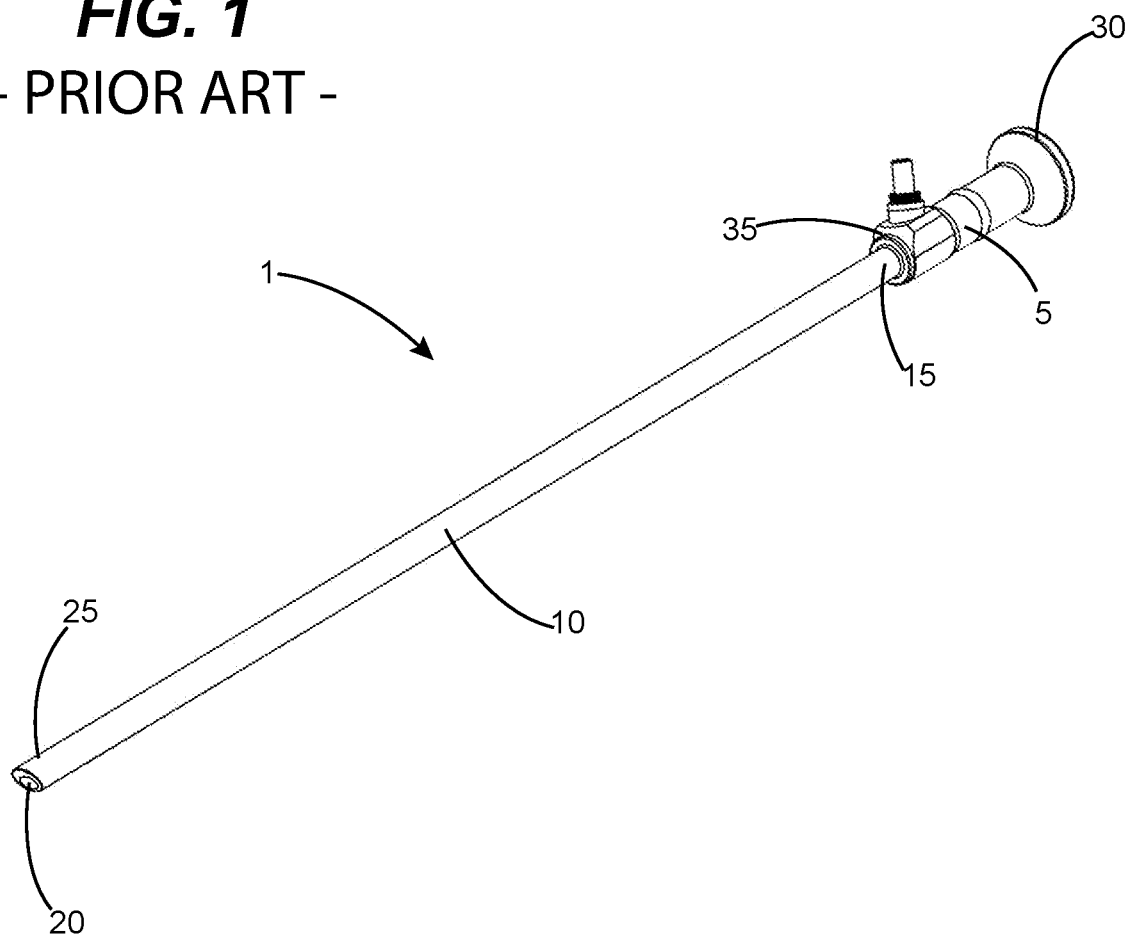
FIG. 1 is a perspective view showing a prior art endoscope.

Embodiments of the present invention provide a method, system and assembly each adapted for enabling an imaging element cleaning apparatus to be placed through an abdominal wall of the patient without the use of a trocar or cannula. By eliminating the need for and use of a cannular or trocar, such embodiments of the present invention advantageously overcome dimensional compatibility issues exhibited between the inside diameter of the central passage of commercially-available trocars and cannulas and the outside diameter of the sheath of an imaging element cleaning apparatus comprising such a sheath. Embodiments of the present invention overcome such dimensional compatibility issues by enabling an imaging element cleaning apparatus of the present disclosures to be placed through the abdominal wall of a patient without the use of a trocar or cannula. As a result, the sheath of the aforementioned imaging element cleaning apparatus can be in direct contact with the abdominal wall tissue (e.g., the fascial tissue) such that direct engagement of the abdominal wall tissue with the exterior surface of the sheath forms a seal (e.g., gas-tight or leak-resistant) therebetween. In this manner, omission of the cannula and trocar eliminates adverse issue associated with dimensional incompatibilities and also eliminates the need to devise a trocar and/or cannula specifically configured for precluding or at least mitigating the aforementioned dimensional incompatibilities.

Turning now to FIGS. 2-3, an endoscope placement assembly 100 comprises a component system including an imaging element cleaning apparatus 105 and an obturator 110. The endoscope cleaning apparatus 105 includes a user interface body 115, a sheath 120 and a cleaning member 125. The sheath 120 includes a central passage 130, best shown in FIG. 4. The cleaning member 125 is located at a distal end portion 135 of the sheath 120. The cleaning member 125 is movably attached to the sheath 120 and is coupled to a control body 140 of the user interface body 115 by a control element 145. Rotation of the control body 140 causes a corresponding rotation of the cleaning member 125 about a longitudinal axis L1 of the control element 145. Such rotation of the cleaning member 125 causes the cleaning member 125 to pass over a central passage opening at the distal end portion 135 of the sheath 120 when the obturator 110 is not mounted on the imaging element cleaning apparatus 105, thereby enabling the cleaning member 125 to clean contaminants and debris from a surface of the imaging element of a device (e.g., lens of an endoscope) when an endoscope is mounted on the imaging element cleaning apparatus 105 in a seated position.

Figure 4:
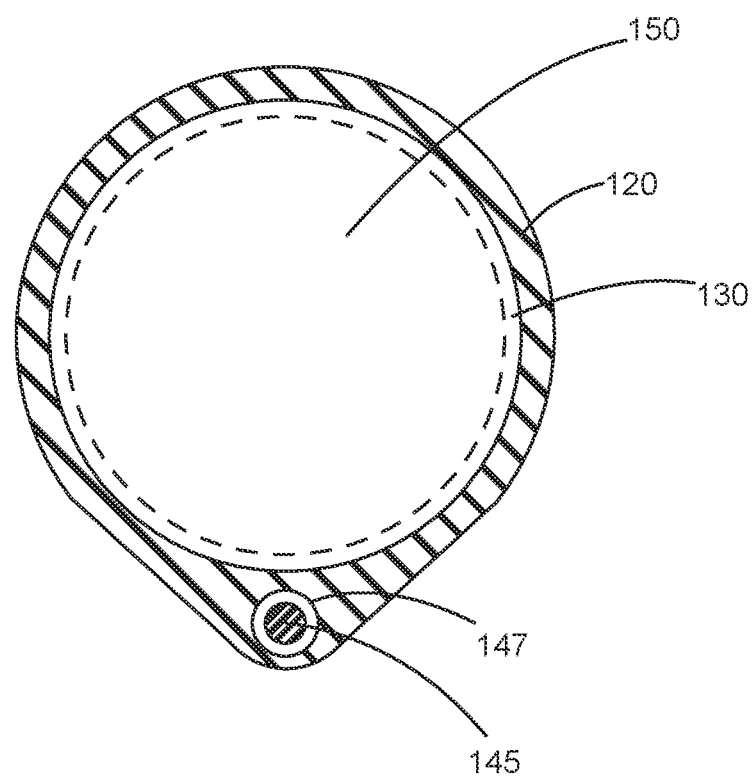
FIG. 4 is a cross-sectional view taken along the line 4-4 in FIG. 3

As shown in FIG. 4, the coupling element 145 extends through a channel 147 within the sheath 120. Preferably, the channel 147 and the central passage 130 extend substantially parallel to each other within the sheath 120. In some embodiments, the coupling element 145 is characterized by an elongated small diameter structure that offers at least a limited degree of bendability in combination with high torsional rigidity. In other embodiments, the coupling element 145 is characterized by an elongated small diameter structure that offers a given amount of torsional compliance. Based on these characterizing attributes, examples of coupling element 145 include, but are not limited to, solid metallic wire, spiraled metal wire, a polymeric filament(s), a composite filament(s) or the like.

A shank 150 of the obturator 110 is slidably disposed within the central passage 130 of the sheath 120, as shown in FIGS. 2-4. For example, in preferred embodiments, an outside diameter of the shank 150 is specified to provide a close-tolerance fit with respect to an inside diameter of the sheath 120, thereby enabling the shank 120 to slide within the central passage 130 of the sheath 120. The obturator 110 is in a seated position S1 on the imaging element cleaning apparatus 105. In the seated position S1, the obturator 110 is at a known position relative to a reference feature of the imaging element cleaning apparatus 105 such that a tip portion 152 of the shank 150 extends from the distal end portion 135 of the sheath 120 by a known (i.e., fixed) amount. A terminal end portion 153 of the shank 150 at least partially defines a tissue penetrating portion of the endoscope placement assembly 110. In one example of the seated position S1, a reference feature of a head 155 of the obturator 110 engages the reference feature of the user interface body 115 (e.g., abutting reference surfaces) for establishing a specified position of the obturator 110 relative to the imaging element cleaning apparatus 105. In preferred embodiments, the head 155 of the obturator 110 includes one or more retention features 157 that each engage a mating retention feature of the user interface body 115 for securing the obturator 110 in the seated position S1 on the imaging element cleaning apparatus 105 until each retention feature 157 of the obturator 110 is selectively released from the mating retention feature 159 of the user interface body 115.

Referring to FIGS. 5 and 6, the shank 150 of the obturator 110 includes a cleaning member receiving receptable 160 at its distal tip portion 152. The cleaning member receiving receptable 160 has a size and a position along a length of the shank 150 for enabling at least a portion of the cleaning member 125 to be disposed therein when the obturator 110 in the seated position S1 on the imaging element cleaning apparatus 105. To this end, the cleaning member 125 can be rotated to a rotational obturator installing position P1 (FIG. 5) in which the obturator 110 can be mounted on the imaging element cleaning apparatus in the seated position without the shank 150 contacting the cleaning member 125 during such mounting—i.e., the shank 150 being slid into the central passage 130 of the sheath 120 until the obturator 110 attains its seated position S1 on the imaging element cleaning apparatus 105. After the obturator 110 is mounted on the imaging element cleaning apparatus 105, the cleaning member 125 is rotated to an assembly use position P2 (FIG. 6) in which at least a portion of the cleaning member 125 is within the cleaning member receiving space 160. The size (e.g., depth) of the cleaning member receiving space 160 and the size of the cleaning member 125 can at least partially determine the extent to which the entire portion of the cleaning member can be disposed within the cleaning member receiving space 160.

The imaging element cleaning apparatus 105 is preferably, but not necessarily, configured to be used with commercially available endoscopes, such as endoscope 1 of FIG. 1. Examples of such commercially available endoscopes include, but are not limited to, endoscopes manufactured under brand names of Karl Storz, Linvatec, Olympus, Richard Wolf, Stryker and Intuitive Surgical (i.e., DaVinci). To this end, in preferred embodiments, cleaning apparatus 105 can be engineered as endoscope-specific for a given model(s) of one or more manufacturers based on the dimensional attributes of such commercially available endoscopes. An underlying consideration of the manner in which the endoscope cleaning apparatus 105 is engineered for an intended brand(s) or model(s) of endoscope is that there be a high level of dimensional precision between the endoscope and the cleaning apparatus. Such dimensional precision can be characterized to include both the inhibition of any unacceptable level of relative movement between the endoscope and the cleaning apparatus 105 and relative placement of key structural elements of the endoscope relative to those of the cleaning apparatus 105.

Advantageously, an endoscope placement assembly in accordance with embodiment of present invention (e.g., the endoscope placement assembly 100 discussed above) enables a unique and beneficial method for enabling an imaging element cleaning apparatus to be operationally placed through the abdominal wall of a patient without the use of a trocar or cannula. As discussed above, eliminating the need for a trocar and/or cannula addresses the aforementioned adverse issues of dimensional compatibility exhibited between the inside diameter of the central passage of commercially-available trocars and cannulas and the outside diameter of the sheath of the imaging element cleaning apparatus. Placement of the imaging element cleaning apparatus in accordance with embodiments of the present invention can result in the sheath of the imaging element cleaning apparatus being in direct contact with the abdominal wall tissue, whereby such direct engagement of abdominal wall tissue with the exterior surface of the sheath forms a gas-tight or leak-resistant seal therebetween.

In one or more embodiments, a method is provided for enabling an imaging element cleaning apparatus in accordance with the disclosure made herein (e.g., the imaging element cleaning apparatus 105 discussed above in reference to FIGS. 2-6) to be operationally placed through an abdominal wall of a patient without the use of a trocar or cannula. To this end, one or more steps are performed for providing an endoscope placement assembly in accordance with one of more embodiments of the present invention (e.g., as referred to in the instant method, the endoscope placement assembly 100 discussed above in reference to FIGS. 2-6). Such steps for providing the endoscope placement assembly 100 can include rotating the cleaning member 125 of the imaging element cleaning apparatus 105 to a rotational obturator installing position P1 (FIG. 5) to enable an obturator 110 to be mounted on the imaging element cleaning apparatus 105 in the seated position S1 without a shank 150 of the obturator 110 inhibiting such mounting (FIG. 5) and then mounting the obturator 110 on the imaging element cleaning apparatus 105 in the seated position S1 while the cleaning member 125 is in the rotational obturator installing position P1. In the case where a cleaning member receiving space 160 of the obturator 110 is in a side surface of a shank 150 (FIGS. 2,3, 5 and 6), one or more steps are next performed for rotating the cleaning member 125 to the assembly use position P2 (FIG. 6) in which the cleaning member 125 is at least partially in the cleaning member receiving space 160. In the case of an obturator where the cleaning member receiving space 160 bisects the distal tip portion 152 of the shank 150 (FIGS. 12 and 13), the assembly use position P2 and the rotational obturator installing position P1 are the same.

Figure 7:
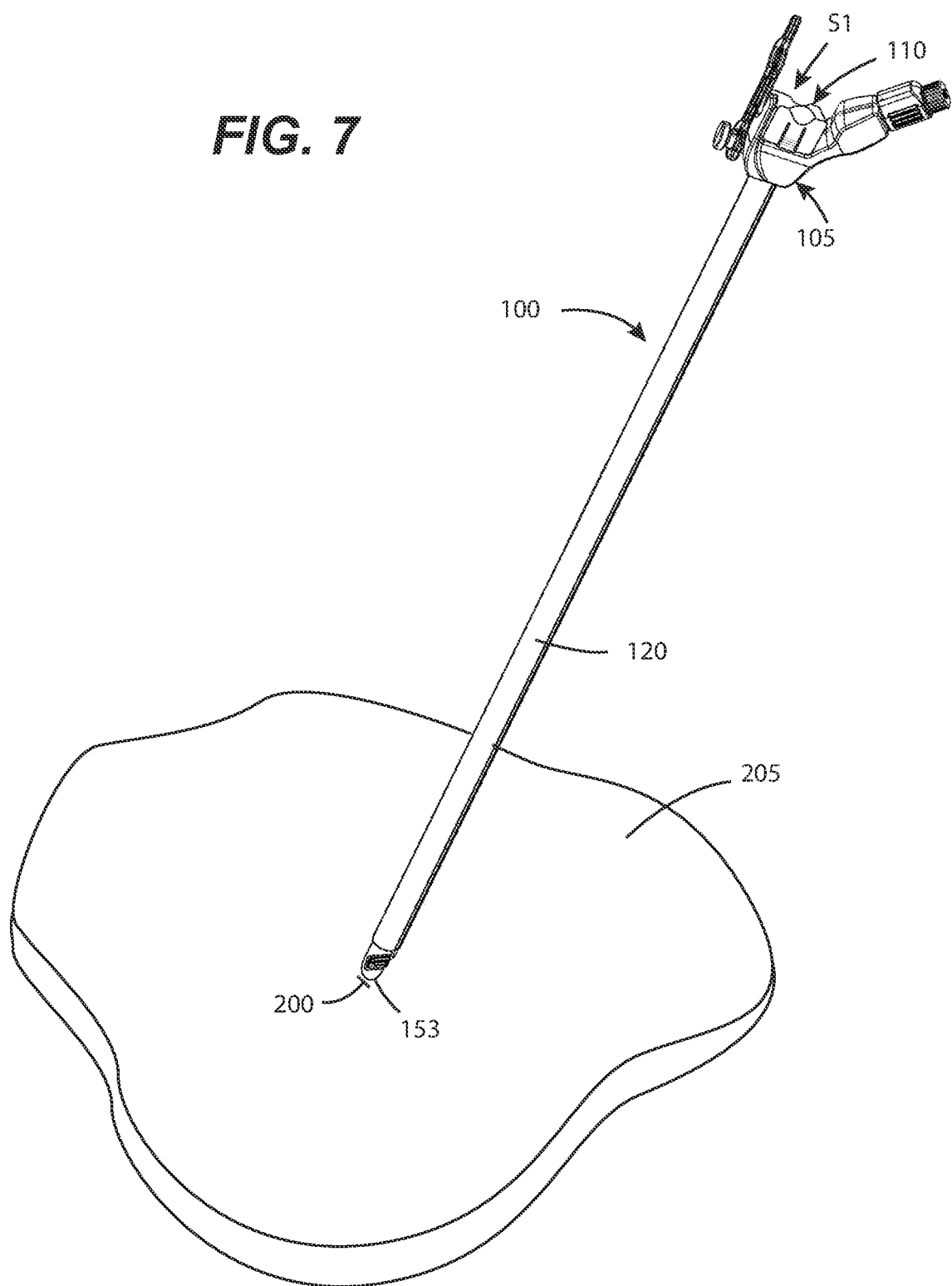
FIG. 7 is a diagrammatic perspective view showing the cleaning apparatus system of FIGS. 2 and 3, with a distal end portion thereof adjacent to a surgical incision with an abdomen wall of a patient.
Figure 8:
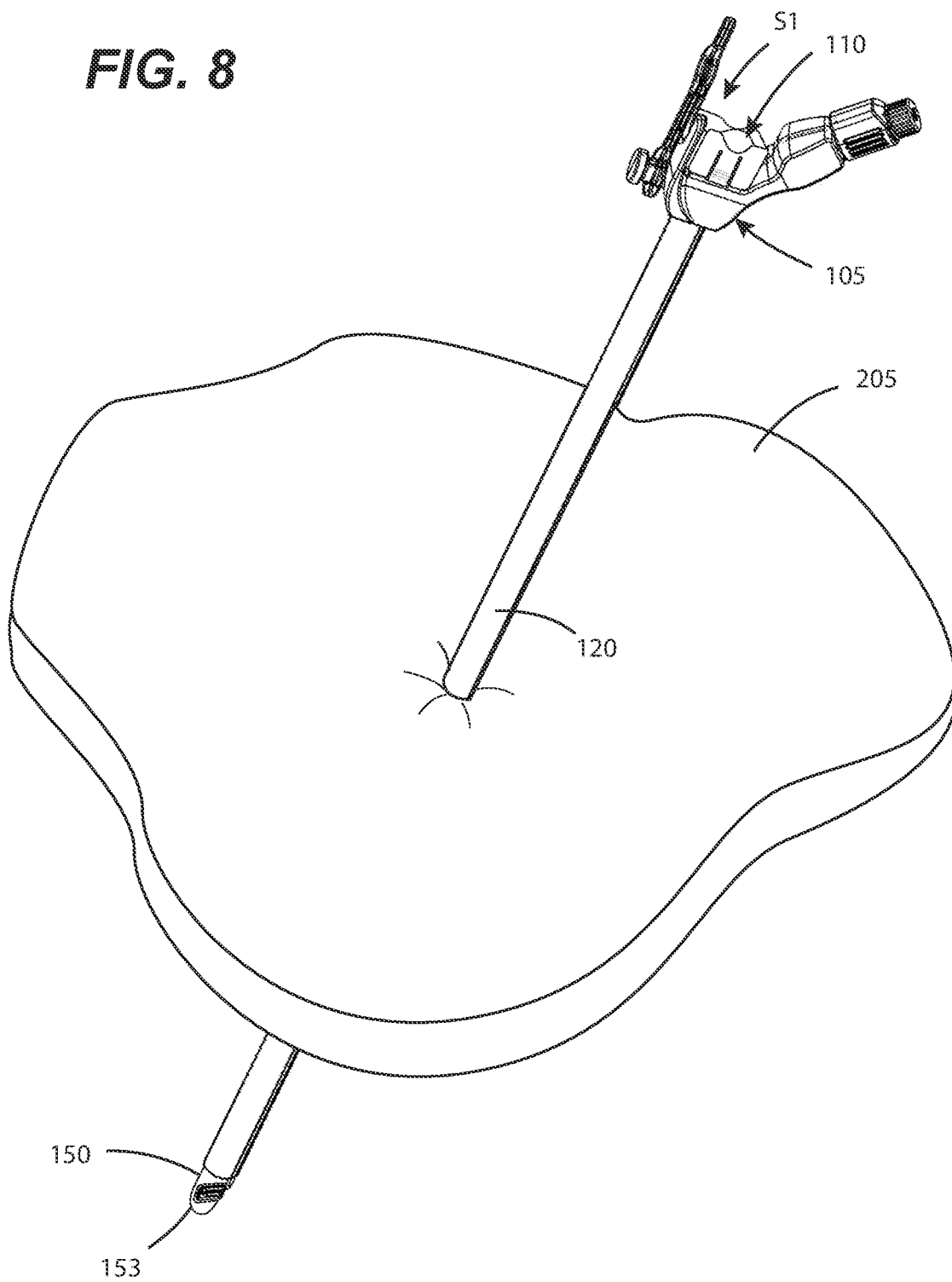
FIG. 8 is a diagrammatic perspective view showing the cleaning apparatus system of FIGS. 2 and 3, showing the distal end portion thereof urged through the abdomen wall of the patient at a location defined by the surgical incision of FIG. 7 and sheath thereof extending through the abdomen wall of the patient.

After providing the endoscope placement assembly 100, one or more steps are performed for forming an incision 200 within an abdominal wall 205 of a patient and engaging the tissue penetrating structure 153 of the endoscope placement assembly 100 with the incision 200, as shown in FIG. 7. Thereafter, as shown in FIG. 8, one or more steps are performed for applying pressure to the endoscope placement assembly 100 to force the tissue penetrating structure 153 through the incision 200 and cause a sheath 120 of the imaging element cleaning apparatus to extend through the abdominal wall, thereby forming direct engagement of tissue of the abdominal wall with the exterior surface of the sheath 120.

As shown in FIG. 9, one or more steps are then performed for detaching the obturator 110 from the imaging element cleaning apparatus 105 and then mating an endoscope 300 with the imaging element cleaning apparatus 105 such that the endoscope 300 is in a seated position S2 on the imaging element cleaning apparatus 105. In the seated position S2, an elongated member 305 of the endoscope 300 is disposed within the central passage 130 of the sheath 120 and a distal end portion 310 of the elongated member 305 protrudes from the distal end portion 135 of the sheath 120. In the seated position S2, the distal end portion 310 of the elongated member 305 and the imaging element 315 that it carries (e.g., a lens) is adjacent to the cleaning member 125. To enhance patient comfort and operative performance, at least a portion of an exterior surface of the sheath 120 can be treated (e.g., coated) to promote low friction engagement with abdominal wall tissue (e.g., with a low-friction polymeric material such a silicone, Teflon™, graphene or the like). The operative functionality of cleaning an imaging element of an endoscope using an imaging element cleaning apparatus equivalent to the imaging element cleaning apparatus 105 disclosure herein is generally known in the art, such as in U.S. patent application Ser. No. 16/593,150; U.S. Pat. Nos. 7,547,314 and 6,923,759 and Japanese Publication No. JP04-362912, all of which are incorporated herein in their entirety by reference (U.S. patent application Ser. No. 16/593,150 is owned by the instant Applicant).

The sheath 120 and the user interface body 115 of the endoscope placement assembly 100 jointly define a chassis of the imaging element cleaning apparatus 105. The chassis serves as the platform on which an endoscope (e.g., a laparoscope) can be mounted in a predictable seated position. It is disclosed herein that the chassis can be that of a robot that provides robot-assisted surgery or can be adapted to operatively interface with a mating mounting portion of such a robot. For example, the sheath 120 and/or the user interface body 115 can be that of an arm or other structure of the robot or adapted to operatively interface with an instrument mounting portion of the arm of the robot.

The sheath 120 can be a tube where the central passage 130 (shown in FIG. 4) has a round or generally round cross-sectional shape. The central passage 130 has a size and profile that is adapted to have the extension portion of the endoscope seated therein by inserting the extension portion into the central passage 130 and sliding the extension portion along the length of the sheath 120 until the endoscope is in a seated position on the chassis.

As shown in FIG. 10, in one or more embodiments, an access site sealing element 400 can be used in conjunction the imaging element cleaning apparatus 105. The access site sealing element 400 can be configured to provide the functionality of mitigating frictional forces from rotation and translational movement of the sheath 120 causing tissue irritation and/or damage at the site where the imaging element cleaning apparatus 105 is placed through the abdominal wall 205. Additionally, the access site sealing element 400 can be configured to limit leakage of gaseous material from within the abdominal cavity, by providing an enhanced gas-tight or leak-resistant seal between the access site sealing element 400 and the abdominal wall 205 and between the sheath 120 and the access site sealing element 400. Such enhanced gas-tight or leak-resistant seal between the access site sealing element 400 and the abdominal wall 205 can be achieved through use of a polymeric material (e.g., silicone rubber, EPDM or the like) and/or a layer of adhesive between that bonds a surface of the access site sealing element 400 to the patient's skin. Such enhanced gas-tight seal between the sheath 120 and the access site sealing element 400a can be achieved through use of a material that readily conforms to and seals against the exterior surface of the sheath 120 (e.g., silicone rubber, EPDM or the like). The access site sealing element 400 can be in the form of a sheet of material having a puncture or other passage forming feature therein or can be a molded article with a passage forming feature or access port formed therein.

Referring now to FIGS. 11-12, a first alternate embodiment of a tissue penetrating structure of an endoscope placement assembly is disclosed. As shown, a cleaning member receiving space 560 is within an end face of the shank 550. The cleaning member receiving space 560 can bisects the distal tip portion 552 of the shank 550. Opposing protruding legs 563, 564 of the shank 550 that are generally of equal length and define therebetween the cleaning member receiving space 560. Interior surfaces of the cleaning member receiving space 560 can follow a contour of a lens wiping portion 526 of the cleaning member 525. In one or more implementations of such an alternate embodiment, a tissue penetrating structure of the endoscope placement assembly can be jointly formed by a rear surface of a cleaning member 525 of an imaging element cleaning apparatus 505 and one or more surfaces of the opposing protruding legs 563, 564. In such implementations, it can be desirable for the rear face of the cleaning member 525 and/or the one or more surfaces of the opposing protruding legs 563, 564 to be shaped to provide an effective tissue penetrating structure—e.g., a pointed shape, a blunt shape or other known shape for a tissue penetrating structure of an obturator.

Referring now to FIG. 13, a second alternate embodiment of a tissue penetrating structure of an endoscope placement assembly is disclosed. As shown, a cleaning member receiving space 660 is within an end face of the shank 650. The cleaning member receiving space 660 can bisects the distal tip portion 652 of the shank 650. Opposing protruding legs 663, 664 of the shank 650 that are of uneven length can define the cleaning member receiving space 660. Interior surfaces of the cleaning member receiving space 660 can follow a contour of a lens wiping portion 626 of the cleaning member 625. In one or more implementations of such an alternate embodiment, a tissue penetrating structure of the endoscope placement assembly can be formed by a longer one of the protruding legs (i.e., protruding leg 664). In such implementations, it is desirable for the longer protruding leg 664 to have a tip that is shaped to provide an effective tissue penetrating structure—e.g., a pointed shape, a blunt shape or other known shape for a tissue penetrating structure of an obturator.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A method, comprising:
   urging a distal tip portion of an obturator of an endoscope placement assembly through an incision within a body cavity wall of a patient until an elongated tubular body of an imaging element cleaning apparatus of the endoscope placement assembly extends through the body cavity wall, wherein a cleaning member of the imaging element cleaning apparatus is located adjacent to a distal end portion of the elongated tubular body, wherein the distal tip portion of the obturator protrudes from within a central passage of the elongated tubular body at the distal end portion thereof and wherein at least a portion of the cleaning member is positioned within a cleaning member receiving space at the distal tip portion of the obturator;
   detaching the obturator from the imaging element cleaning apparatus; and
   after detaching the obturator, adjoining an endoscope with the imaging element cleaning apparatus for enabling the cleaning member to perform cleaning of an imaging element of the endoscope.

2. The method of claim 1 wherein:
   the method further comprises forming the endoscope placement assembly;
   at least a portion of the cleaning member receiving space is within one of a side surface of a shank of the obturator and an end face of the shank; and
   forming the endoscope placement assembly comprises positioning the at least a portion of the cleaning member within the cleaning member receiving space after inserting the shank into the central passage of the elongated tubular body.

3. The method of claim 1 wherein:
   the method further comprises forming the endoscope placement assembly;
   at least a portion of the cleaning member receiving space is within a side surface of a shank of the obturator; and
   forming the endoscope placement assembly comprises:
      rotating the cleaning member of the imaging element cleaning apparatus to a rotational obturator installing position;
      inserting the shank into the central passage of the elongated tubular body for causing the distal tip portion of the shank to protrude from within the central passage of the elongated tubular body at a distal end portion thereof; and
      rotating the cleaning member to an assembly use position in which the at least a portion of the cleaning member is within the cleaning member receiving space.

4. The method of claim 3 wherein detaching the obturator from the imaging element cleaning apparatus includes:
   rotating the cleaning member to an obturator detachment position in which the shank can be withdrawn from within the central passage of the elongated tubular body without the shank contacting the cleaning member during said withdrawal of the shank; and
   removing the shank from within the central passage.

5. The method of claim 1 wherein:
   the method further comprises forming the endoscope placement assembly;
   at least a portion of the cleaning member receiving space is within an end face of a shank of the obturator; and forming the endoscope placement assembly comprises:
  positioning the cleaning member in front of a central passage of the elongated tubular body; and
  inserting the skank of the obturator into the central passage until at least a portion of the cleaning member is within the cleaning member receiving space.

6. The method of claim 1 wherein:
a surface of the cleaning member at least partially defines a tissue penetrating structure of the endoscope placement assembly; and
urging the distal end portion of the obturator through the incision includes engaging the tissue penetrating structure of the endoscope placement assembly with the incision.

7. The method of claim 6 wherein:
the method further comprises forming the endoscope placement assembly;
at least a portion of the cleaning member receiving space is within an end face of a shank of the obturator; and
forming the endoscope placement assembly comprises:
  positioning the cleaning member in front of a central passage of the elongated tubular body; and
  inserting the skank of the obturator into the central passage until at least a portion of the cleaning member is within the cleaning member receiving space.

8. The method of claim 1 wherein the method further comprises:
  applying an access site sealing element to an exterior surface of the body cavity wall; and
  forming the incision through the access site sealing element.

9. The method of claim 8 wherein:
a surface of the cleaning member at least partially defines a tissue penetrating structure of the endoscope placement assembly; and
urging the distal end portion of the obturator through the incision includes engaging the tissue penetrating structure of the endoscope placement assembly with the incision.

10. The method of claim 9 wherein:
the method further comprises forming the endoscope placement assembly;
at least a portion of the cleaning member receiving space is within an end face of a shank of the obturator; and
forming the endoscope placement assembly comprises:
  positioning the cleaning member in front of the central passage of the elongated tubular body; and
  inserting the skank of the obturator into the central passage until at least a portion of the cleaning member is within the cleaning member receiving space.

11. A method, comprising:
forming an incision within a body cavity wall of a patient;
engaging a tissue penetrating structure of an endoscope placement assembly with the incision, wherein the endoscope placement assembly comprises an imaging element cleaning apparatus and an obturator, wherein a shank of the obturator positioned is within a central passage of a sheath of the imaging element cleaning apparatus, wherein a distal tip portion of the shank protrudes from within the central passage of the sheath at a distal end portion thereof and wherein at least a portion of a cleaning member of the imaging element cleaning apparatus is positioned within a cleaning member receiving space at the distal tip portion of the shank;
urging the tissue penetrating structure through the incision until the sheath extends through the body cavity wall;
detaching the obturator from the imaging element cleaning apparatus; and
after detaching the obturator, adjoining an endoscope with the imaging element cleaning apparatus for enabling the cleaning member to perform cleaning of an imaging element of the endoscope.

12. The method of claim 11 wherein:
the method further comprises forming the endoscope placement assembly;
forming the endoscope placement assembly comprises:
  inserting the shank into the central passage; and
  in conjunction with or after inserting the shank into the central passage, causing the at least a portion of the cleaning member to become positioned within the cleaning member receiving space.

13. The method of claim 11 wherein:
at least a portion of the cleaning member receiving space is within a side surface of the shank;
the method further comprises forming the endoscope placement assembly; and
forming the endoscope placement assembly comprises:
  rotating the cleaning member of the imaging element cleaning apparatus to a rotational obturator installing position;
  inserting the shank into the central passage of the sheath; and
  rotating the cleaning member to an assembly use position in which the at least a portion of the cleaning member is within the cleaning member receiving space.

14. The method of claim 13 wherein:
detaching the obturator from the central passage of the sheath includes:
  rotating the cleaning member to an obturator detachment position in which the shank can be withdrawn from within the central passage of the sheath without the shank contacting the cleaning member during said withdrawal of the shank; and
  removing the shank from within the central passage of the sheath.

15. The method of claim 11 wherein:
at least a portion of the cleaning member receiving space is within an end face of the shank;
the method further comprises forming the endoscope placement assembly; and
forming the endoscope placement assembly comprises:
  position the cleaning member in front of the central passage of the sheath; and
  inserting the skank of the obturator into the central passage of the sheath until at least a portion of the cleaning member is within the cleaning member receiving space.

16. The method of claim 11 wherein:
a surface of the cleaning member at least partially defines a tissue penetrating structure of the endoscope placement assembly; and
urging the tissue penetrating structure through the incision includes engaging the tissue penetrating structure with the incision.

17. The method of claim 11 wherein the method further comprises:

applying an access site sealing element to an exterior surface of the body cavity wall; and forming the incision through the access site sealing element.

18. The method of claim 17 wherein:

the method further comprises forming the endoscope placement assembly;

forming the endoscope placement assembly comprises:
  inserting the shank into the central passage; and
  in conjunction with or after inserting the shank into the central passage, causing the at least a portion of the cleaning member to become positioned within the cleaning member receiving space.

19. The method of claim 18 wherein:

at least a portion of the cleaning member receiving space is within a side surface of the shank;

the method further comprises forming the endoscope placement assembly; and forming the endoscope placement assembly comprises:
  rotating the cleaning member of the imaging element cleaning apparatus to a rotational obturator installing position;
  inserting the shank into the central passage of the sheath; and
  rotating the cleaning member to an assembly use position in which the at least a portion of the cleaning member is within the cleaning member receiving space.

20. The method of claim 18 wherein:

at least a portion of the cleaning member receiving space is within an end face of the shank;

the method further comprises forming the endoscope placement assembly; and forming the endoscope placement assembly comprises:
  position the cleaning member in front of the central passage of the sheath; and
  inserting the skank of the obturator into the central passage of the sheath until at least a portion of the cleaning member is within the cleaning member receiving space.

* * * * *